(12) United States Patent
Sim et al.

(10) Patent No.: US 8,934,032 B2
(45) Date of Patent: Jan. 13, 2015

(54) PRINTED AUDIO FORMAT AND PHOTOGRAPH WITH ENCODED AUDIO

(75) Inventors: Wong Hoo Sim, Singapore (SG); Desmond Toh Onn Hii, Singapore (SG); Tur Wei Chan, Singapore (SG); Chin Fang Lim, Singapore (SG); Willie Png, Singapore (SG); Morgun Phay, Singapore (SG)

(73) Assignee: Creative Technology Ltd, Singapore (SG)

(*) Notice: Subject to any disclaimer, the term of this patent is extended or adjusted under 35 U.S.C. 154(b) by 579 days.

(21) Appl. No.: 12/915,565

(22) Filed: Oct. 29, 2010

(65) Prior Publication Data

US 2011/0043832 A1 Feb. 24, 2011

Related U.S. Application Data

(62) Division of application No. 11/016,333, filed on Dec. 17, 2004, now Pat. No. 7,847,835.

(60) Provisional application No. 60/531,471, filed on Dec. 19, 2003.

(51) Int. Cl.
*H04N 5/76* (2006.01)
*G06F 17/00* (2006.01)
(Continued)

(52) U.S. Cl.
CPC .............. *G03B 31/00* (2013.01); *A61K 31/355* (2013.01); *A61K 31/375* (2013.01); *A61K 33/30* (2013.01);
(Continued)

(58) Field of Classification Search
CPC ................................................. H04N 1/00326

USPC ........... 348/207.1, 231, 231.4, 222.1; 700/94; 396/312
See application file for complete search history.

(56) References Cited

U.S. PATENT DOCUMENTS 3,093,709 A * 6/1963 Hoshino et al. ................. 360/17
3,439,598 A 4/1969 Weitzner et al.
(Continued)

FOREIGN PATENT DOCUMENTS

JP 2003348327 12/2003
JP 2003348327 A2 12/2003
(Continued)

OTHER PUBLICATIONS

"U.S. Appl. No. 09/703,510, Advisory Action mailed Jul. 13, 2004", 3 pgs.
(Continued)

*Primary Examiner* — Twyler Haskins
*Assistant Examiner* — Akshay Trehan
(74) *Attorney, Agent, or Firm* — Schwegman Lundberg & Woessner, P.A.

(57) ABSTRACT

A printed audio format includes a printed encoding of an audio signal, and a plurality of spaced-apart and parallel rails. The printed encoding of the audio signal is located between the plurality of rails and each rail comprises at least one marker. The printed encoding comprises a first portion and a second portion, each portion comprises a plurality of code frames, and each frame represents a time segment of an audio signal. The first portion encodes a first time period of the audio signal and the second portion encodes a second time period of the audio signal. The second portion is encoded in reverse order with respect to the first portion so that the joining part is on the same end of both portions.

19 Claims, 15 Drawing Sheets

(51) Int. Cl.

| | | |
|---|---|---|
| *G03B 17/24* | (2006.01) | |
| *G03B 31/00* | (2006.01) | |
| *A61K 31/355* | (2006.01) | |
| *A61K 31/375* | (2006.01) | |
| *A61K 33/30* | (2006.01) | |
| *H04N 1/00* | (2006.01) | |
| *H04N 1/32* | (2006.01) | |
| *H04N 101/00* | (2006.01) | |

(52) U.S. Cl.
CPC ....... *H04N 1/00326* (2013.01); *H04N 1/32133* (2013.01); *H04N 1/32144* (2013.01); *H04N 2101/00* (2013.01); *H04N 2201/0084* (2013.01); *H04N 2201/3264* (2013.01); *H04N 2201/3269* (2013.01); *H04N 2201/3271* (2013.01); *H04N 2201/328* (2013.01); *H04N 2201/3283* (2013.01)
USPC .......................... 348/231.4; 700/94; 396/312

(56) References Cited

U.S. PATENT DOCUMENTS

| | | | |
|---|---|---|---|
| 4,983,996 | A | 1/1991 | Kinoshita |
| 5,014,078 | A | 5/1991 | Kudo et al. |
| 5,247,330 | A | 9/1993 | Ohyama et al. |
| 5,276,472 | A | 1/1994 | Bell et al. |
| 5,313,235 | A | 5/1994 | Inoue et al. |
| 5,313,564 | A | 5/1994 | Kafri et al. |
| 5,363,157 | A | 11/1994 | Cocca |
| 5,369,261 | A | 11/1994 | Shamir |
| 5,389,989 | A | 2/1995 | Hawkins et al. |
| 5,485,241 | A | 1/1996 | Irie et al. |
| 5,521,663 | A | 5/1996 | Norris |
| 5,801,848 | A | 9/1998 | Kafri |
| 5,863,209 | A | 1/1999 | Kim |
| 5,867,593 | A | 2/1999 | Fukuda et al. |
| 5,896,403 | A | 4/1999 | Nagasaki et al. |
| 5,897,669 | A | 4/1999 | Matsui |
| 5,996,893 | A | 12/1999 | Soscia |
| 5,999,899 | A | 12/1999 | Robinson |
| RE36,589 | E | 2/2000 | Akamine et al. |
| 6,044,348 | A | 3/2000 | Imade et al. |
| 6,163,656 | A | 12/2000 | Yoshioka |
| 6,229,964 | B1 | 5/2001 | Bell |
| 6,247,649 | B1 | 6/2001 | Nada |
| 6,322,181 | B1 | 11/2001 | Silverbrook |
| 6,332,030 | B1 | 12/2001 | Manjunath et al. |
| 6,377,309 | B1 * | 4/2002 | Ito et al. .................. 348/554 |
| 6,388,681 | B1 | 5/2002 | Nozaki |
| 6,440,497 | B1 * | 8/2002 | Hohenstein ................ 427/256 |
| 6,460,155 | B1 * | 10/2002 | Nagasaki et al. .......... 714/752 |
| 6,466,262 | B1 | 10/2002 | Miyatake et al. |
| 6,618,511 | B1 | 9/2003 | Mancuso et al. |
| 7,179,982 | B2 | 2/2007 | Goto |
| 7,248,934 | B1 * | 7/2007 | Rossum et al. ............ 700/94 |
| 7,847,835 | B2 | 12/2010 | Sim et al. |
| 8,442,262 | B2 | 5/2013 | Sim et al. |
| 2001/0052542 | A1 * | 12/2001 | Matsueda et al. ........ 235/435 |
| 2002/0057457 | A1 | 5/2002 | Nozaki et al. |
| 2002/0159653 | A1 | 10/2002 | Dekel et al. |
| 2003/0015587 | A1 | 1/2003 | Tsikos et al. |
| 2003/0048946 | A1 | 3/2003 | Foote et al. |
| 2004/0068399 | A1 * | 4/2004 | Ding ........................ 704/200.1 |
| 2004/0200337 | A1 | 10/2004 | Abe et al. |
| 2005/0041120 | A1 | 2/2005 | Miller |
| 2005/0185069 | A1 | 8/2005 | Sim et al. |
| 2005/0241465 | A1 | 11/2005 | Goto |

FOREIGN PATENT DOCUMENTS

| | | |
|---|---|---|
| JP | 2004153737 | 5/2004 |
| JP | 2004153737 A2 | 5/2004 |
| JP | 2004163485 | 6/2004 |
| JP | 2004163485 A2 | 6/2004 |
| JP | 2004173172 | 6/2004 |
| JP | 2004173172 A2 | 6/2004 |
| WO | WO-9955037 A1 | 10/1999 |
| WO | WO-0217214 A2 | 2/2002 |

OTHER PUBLICATIONS

"U.S. Appl. No. 09/703,510, Final Office Action mailed Apr. 7, 2004", 6 pgs.
"U.S. Appl. No. 09/703,510, Final Office Action mailed Jul. 12, 2006", 18 pgs.
"U.S. Appl. No. 09/703,510, Final Office Action mailed Aug. 19, 2005", 17 pgs.
"U.S. Appl. No. 09/703,510, Non-Final Office Action mailed Feb. 8, 2006", 16 pgs.
"U.S. Appl. No. 09/703,510, Non-Final Office Action mailed Oct. 24, 2003", 13 pgs.
"U.S. Appl. No. 09/703,510, Non-Final Office Action mailed Nov. 3, 2004", 16 pgs.
"U.S. Appl. No. 09/703,510, Notice of Allowance mailed Mar. 16, 2007", 4 pgs.
"U.S. Appl. No. 09/703,510, Response filed Jan. 22, 2004 to Non-Final Office Action mailed Oct. 24, 2003", 16 pgs.
"U.S. Appl. No. 09/703,510, Response filed Feb. 1, 2005 to Non-Final Office Action mailed Nov. 3, 2004", 13 pgs.
"U.S. Appl. No. 09/703,510, Response filed May 1, 2006 to Non-Final Office Action mailed Feb. 8, 2006", 9 pgs.
"U.S. Appl. No. 09/703,510, Response filed Jun. 3, 2004 to Final Office Action mailed Apr. 7, 2004", 10 pgs.
"U.S. Appl. No. 09/703,510, Response filed Nov. 13, 2006 to Final Office Action mailed Jul. 12, 2006", 15 pgs.
"U.S. Appl. No. 11/016,333 Notice of Allowance mailed Sep. 7, 2010", 10 pgs.
"U.S. Appl. No. 11/016,333, Response filed Jul. 16, 2010 to Non Final Office Action mailed Apr. 16, 2010", 10 pgs.
"U.S. Appl. No. 11/016,333, Advisory Action mailed Feb. 26, 2010", 2 pgs.
"U.S. Appl. No. 11/016,333, Final Office Action mailed Dec. 11, 2009", 16 pgs.
"U.S. Appl. No. 11/016,333, Non-Final Office Action mailed May 12, 2009", 14 pgs.
"U.S. Appl. No. 11/016,333, Non-Final Office Action mailed Apr. 16, 2010", 16 pgs.
"U.S. Appl. No. 11/016,333, Response filed Feb. 11, 2010 to Final Office Action mailed Dec, 11, 2009", 13 pgs.
"U.S. Appl. No. 11/016,333, Response filed Apr. 24, 2009 to Restriction Requirement mailed Feb. 26, 2009", 6 pgs.
"U.S. Appl. No. 11/016,333, Response filed Aug. 5, 2009 to Non Final Office Action mailed May 12, 2009", 11 pgs.
"U.S. Appl. No. 11/016,333, Restriction Requirement mailed Feb. 26, 2009", 6 pgs.
"U.S. Appl. No. 11/016,366, Advisory Action mailed Feb, 24, 2010", 3 pgs.
"U.S. Appl. No. 11/016,366, Final Office Action mailed Nov. 30, 2009", 13 Pgs.
"U.S. Appl. No. 11/016,366, Non-Final Office Action mailed Apr. 14, 2009", 29 pgs.
"U.S. Appl. No. 11/016,366, Response filed Jan. 19, 2009 to Restriction Requirement mailed Jan. 7, 2009", 10 pgs.
"U.S. Appl. No. 11/016,366, Response filed Feb. 1, 2010 to Final Office Action mailed Nov. 30, 2009", 11 pgs.
"U.S. Appl. No. 11/016,366, Response filed Oct. 14, 2008 to Restriction Requirement mailed Sep. 30, 2008", 9 pgs.
"U.S. Appl. No. 11/016,366, Response filed Jul. 30, 2009 Non Final Office Action mailed Apr. 14, 2009", 11 pgs.
"U.S. Appl. No. 11/016,366, Restriction Requirement mailed Jan. 7, 2009", 8 pgs.
"U.S. Appl. No. 11/016,366, Restriction Requirement mailed Sep. 30, 2008", 6 pgs.
"International Application Serial No. PCT/SG2004/000419, International Preliminary Report on Patentability mailed Nov. 11, 2005", 7 pgs.

(56) References Cited

OTHER PUBLICATIONS

"International Application Serial No. PCT/SG2004/000419, International Search Report mailed Mar. 9, 2005", 4 pgs.
"Terminal Equipment and Protocols for Telematic Services: Information Technology—Digital Compression and Coding of Continuous-Tone Still Images—Requirements and Guidelines", International Telecommunication Union Recommendation T.81, (1993), 186 pages.
Chae, J. J., et al., "A Technique for Image Data Hiding and Reconstruction without Host Image", Proceedings of the SPIE 3657, San Jose, CA, (Jan. 1999), 386-396.
Chen, Brian, et al., "Quantization Index Modulation: A Class of Provably Good Methods for Digital Watermarking and Information Embedding", IEEE Transactions on Information Theory, 47(4), (May 2001), 1423-1443.
Cho, Youngkwan, et al., "Multiring Fiducial Systems for Scalable Fiducial-Tracking Augmented Reality", Presence, 10(6), (Dec. 6, 2001), 599-612.
Conway, J. J., et al., "Fast quantizing and decoding and algorithms for lattice quantizers and codes", IEEE Transactions in Information Theory, 28(2), (Mar. 1982), 227-232.
Conway, John H., et al., "Sphere Packings, Lattices and Groups", New York : Springer-Verlag, 2nd Edition—Book, (1993), 679 Pages.
Giannoula, A., et al., "Compressive Data Hiding for Video Signals", Proc. 2003 International Conference on Image Processing, (Sep. 2003), 529-32.
Giannoula, A., et al., "Integrating Compression with Watermarking on Video Sequences", Proc. 2004 International Conference on Information Technology, (Apr. 2004), 159-60.
Gortler, Steven J., et al., "The Lumigraph", International Conference on Computer Graphics and Interactive Techniques, Proceedings of the 23rd annual conference on Computer graphics and interactive techniques, (1996), 43-54.
Griffin, Daniel, "Signal Estimation from Modified Short-Time Fourier Transform", IEEE Transactions on Acoustics, Speech, and Signal Processing, vol. ASSP-32, No. 2, (Apr. 1984), 236-243.
Jacobsen, N., et al., "Image Adaptive High Volume Data Hiding Based on Scalar Quantization", IEEE MILCOM 2002. Proceedings, vol. 1, (Oct. 7-10, 2002), 411-415.

Mukherjee, D., et al., "A source and channel-coding framework for vector-based data hiding in video", IEEE Trans. on Circuits and Systems for Video Technology, 10(4), (Jun. 2000), 630-645.
Mukherjee, Debargha, et al., "A Source and Channel Coding Approach to Data Hiding with Application to Hiding Speech in Video", Proc. 1998 International Conference on Image Processing, (Oct. 1998), 348-52.
Pennebaker, William B, et al., "JPEG: Still Image Data Compression Standard", New York : Van Nostrand Reinhold, Book, (1993), 638 Pages.
Princen, John, "Analysis/Synthesis Filter Bank Design Based on Time Domain Aliasing Cancellation", IEEE Transactions on Acoustics, Speech, and Signal Processing, vol. ASSP-35, No. 5, (Oct. 1986), 1153-1161.
Rubin, Philip, "The Pattern Playback", http://www.haskins.yale.edu/haskins/MISC/PP/pp.html, (Nov. 10, 2203), 5 pages.
Solanki, K., et al., "High-volume data hiding in images: Introducing perceptual criteria into quantization based embedding", Proceedings of ICASSP, (May 2002), 1-4.
Swanson, Mitchell D., et al., "Data Hiding for Video-in-Video", Proc. 1997 International Conference on Image Processing, (Oct. 1997), 676-9.
Swanson, Mitchell D., et al., "Multimedia Data-Embedding and Watermarking Technologies", Proc. IEEE (Special Issue on Multimedia Signal Processing) 86(6), (Jun. 1998), 1064-87.
Vail, Mark, "Keyboard Reports: MetaSynth Bundle", http://www.keyboardonline.com/demos/metashythbundle/index.shtml.
Wolfgang, Raymond B., et al., "Perceptual Watermarks for Digital Images and Video", Proceedings of the IEEE, 87(7), (Jul. 1999), 1108-1126.
"U.S. Appl. No. 09/703,510, Response filed Nov. 21, 2005 to Final Office Action mailed Aug. 19, 2005", 14 pgs.
"U.S. Appl. No. 11/016,366, Final Office Action mailed Oct. 6, 2011", 14 pgs.
"U.S. Appl. No. 11/016,366, Non Final Office Action mailed Apr. 11, 2011", 13 pgs.
"U.S. Appl. No. 11/016,366, Notice of Allowance mailed Jan. 11, 2013", 10 pgs.
"U.S. Appl. No. 11/016,366, Response filed Feb. 6, 2012 to Final Office Action mailed Oct. 6, 2011", 13 pgs.
"U.S. Appl. No. 11/016,366, Response filed Jul. 20, 2011 to Non-Final Office Action mailed Apr. 11, 2011", 9 pgs.

\* cited by examiner

STANDARD THRESHOLD
FOR POSITION X

TOP PIXEL BLACK THRESHOLD
FOR POSITION X

LEFT PIXEL BLACK THRESHOLD
FOR POSITION X

TOP AND LEFT PIXEL BLACK
THRESHOLD FOR POSITION X

PRINTED AUDIO FORMAT AND PHOTOGRAPH WITH ENCODED AUDIO

RELATED APPLICATIONS

This application is a divisional patent application filed under 37 C.F.R. 1.53(b) and claims the benefit of U.S. patent application Ser. No. 11/016,033 entitled "Still Camera with Audio Decoding and Coding, a Printable Audio Format, and Method" filed Dec. 17, 2004 under 35 U.S.C. 121, which claimed priority benefit from U.S. Provisional Patent Application 60/531,471 entitled "Still Camera with Audio Decoding and Coding, a Printable Audio Format, and Method" filed on Dec. 19, 2003, the contents of which is incorporated herein by reference.

FIELD OF THE INVENTION

This invention relates to a digital still camera with audio decoding and encoding, a printable audio format, and corresponding methods and refers particularly, though not exclusively, to such a digital still camera able to be used to decode previously encoded audio, and for encoding the audio; as well as a printable audio format for the encoded audio.

BACKGROUND TO THE INVENTION

There have been many proposals for encoding audio associated with an image such as, for example, a photographic image, or a document, to enable the encoded audio to be printed as an audio format with, or for application to, the image or document. Subsequently, a scanner is used to scan the printed audio format to enable the encoded audio to be decoded, and reproduced. This requires a separate scanner able to communicate with a sound reproducing system, or to download the scanned data into a sound reproducing system. Such scanners are also prone to errors in reading the printed audio format, as they are hand operated.

SUMMARY OF THE INVENTION

In accordance with a preferred aspect there is provided a digital still camera, comprising:
- a photographic imaging system for capturing a single photographic image of printed material containing a printed audio format;
- a processor for extracting encoded audio data from the photographic image;
- a decoder for receiving and decoding the encoded audio data to an audio signal; and
- an audio output for outputting the audio signal as audio.

In a further preferred aspect, there is provided a digital still camera for reproduction of an audio signal encoded in a printable audio format, the digital still camera comprising:
- a photographic imaging system for capturing a single still photographic image of printed material containing a printed audio format;
- a processor for extracting encoded audio data from the single still photographic image;
- a decoder for receiving and decoding the encoded audio data to an audio signal; and
- data storage for storage of at least one of the audio signal and the encoded audio data.

For both aspects, data storage for storage of at least one of the encoded audio data and the audio signal may be provided, and the decoder/encoder may encode and decode using at least one of Short Term Fourier Transform and Code Excitation Linear Prediction.

The digital still camera may further include a first light source for producing a first light beam directable to a required location to locate a lens of the digital still camera a prescribed distance from the required location relative to the printed audio format. Alternatively, the digital still camera may further comprise a second light source spaced from the first light source and being for producing a second light beam directable to the required location, the first and second light beams being co-incident on the required location when the lens is the prescribed distance from the printed audio format.

There may be a third light source spaced from both the first and the second light sources, and being for producing a third light beam directable to the required location; the first, second and third light beams being substantially co-incident on the required location when the lens is the prescribed distance from and parallel to the printed audio format. Alternatively, all three light beams may originate from a single source and may focus on three different points.

Further alternatively, there may be an attachment to enable a lens of the digital still camera to be located a prescribed distance from and parallel to a required location relative to the printed audio format, the attachment comprising a frame to which the camera can be attached such that the camera is at a fixed position the prescribed distance above the printed. The frame may comprise a base having an opening through which the lens can capture the image, and a plurality of side walls extending from the base for the prescribed distance. At least one of the plurality of side walls may include at least one light source for illuminating the printed audio format. The at least one light source may be remote from the digital still camera so as to be outside a visible region of the lens.

The frame may comprise a base having an opening through which the lens can capture the image, and a plurality of legs extending from the base for the prescribed distance.

The digital still camera may further comprise a view finder comprising a view finder frame, the view finder frame comprising a plurality of frame guides for placement on required locations of an image of the printed audio format when the digital still camera is substantially correctly located relative to the printed audio format.

The digital still camera may further comprise an audio output for output of the audio signal as audio.

The digital still camera may further comprise an amplifier for amplifying the audio signal, and a converter for converting digital audio to analog audio. The audio output may be selected from a loudspeaker; and an output socket for earphone or headphones.

The imaging system may also be for taking photographs and may include an image capturing device. There may also be provided at least one microphone for capturing an audio signal associated with a photograph, and a converter for converting analog audio to digital audio. The decoder may also be an encoder for encoding the input digital audio signal into encoded input audio data able to be printed in a printable audio format.

The processor may embed the encoded input audio data into an associated photograph such that printing of the photograph will result in the encoded input audio data being printed therewith as a printed audio format. The encoded input audio data together with the associated photograph may be stored in a data storage without embedding the encoded audio data into the associated photograph. The digital still camera may further comprise a printer for printing the printable audio format.

The encoded input audio data may be stored separately from the photograph and have a data connection to the photograph.

The microphone may be selected from built-in to the camera, and separate from the camera but operatively connectable to the camera.

The decoder/encoder may encode and decode using at least one of Short Term Fourier Transform and Code Excitation Linear Prediction.

In another preferred aspect there is provided a method of reproducing an audio signal encoded in a printed audio format, the method comprising:
  placing a digital still camera adjacent the printed audio format with a lens of the digital still camera directed towards the printed audio format, the printed audio format being within a focal range of the lens;
  capturing a single still photographic image of the printed audio format in the digital still camera;
  processing the single still photographic image of the printed audio format in the digital still camera to produce printed audio format image data;
  processing the printed audio format image data to obtain an audio signal; and
  reproducing the audio signal as audible audio.

In yet another preferred aspect there is provided a method of sound reproduction of an audio signal encoded in a printable audio format, the method comprising the steps:
  capturing a single still photographic image of the printable audio format using a digital still camera;
  processing the single still photographic image to extract therefrom a data signal corresponding to the audio signal;
  converting the data signal to the audio signal; and
  reproducing the audio signal.

The processing of the printed audio format may comprise:
  retrieving an audio tag from the printed audio image data;
  searching a database of stored audio for a stored audio with the same audio tag;
  if the stored audio with the audio tag is found, retrieving the stored audio and using the stored audio as the audio signal.

Alternatively, the processing of the printed audio format may comprise:
  extracting encoded audio data from the image;
  decoding the encoded audio data to a digital audio signal;
  converting the digital audio signal to an analog audio signal.

At least one of the encoded audio data and the digital audio signal may be stored.

For both methods, the data signal and the digital audio signal may be stored, and the digital audio signal and the audio signal may be amplified. The decoding may be by using at least one of Short Term Fourier Transform and Code Excitation Linear Prediction.

The capturing may comprise:
  locating at least three centre rail markers of the printed audio format;
  validating at least three centre markers;
  locating the rest of the markers on the centre rail; and
  sorting all centre markers.

The locating of the at least three centre markers may comprise: searching for the at least three markers in a centre region and, upon the location of the at least three markers, examining a position of all remaining markers is examined. A block-matching search may be performed.

If the search in the centre region fails, searching continues in an upper region and, if the search in the upper region also fails, searching continues in a bottom region. If the search in all three regions fails a blind decode is performed. The upper region, centre region, and bottom region are all pre-defined.

In yet a further preferred aspect there is provided a method of sound reproduction of an audio signal encoded in a printable audio format, the method comprising:
  capturing a single still photographic image of the printable audio format using a digital still camera;
  processing the single still photographic image to extract therefrom a data signal corresponding to the audio signal;
  retrieving an audio tag from the printed audio image data;
  searching a database of stored audio for a stored audio with the same audio tag; and
  if the stored audio with the audio tag is found, retrieving the stored audio reproducing the stored audio.

A yet further aspect provides a printable audio format comprising:
  a printed encoding of an audio signal;
  a plurality of spaced-apart and parallel rails;
  the printed encoding of the audio signal being located between the plurality of rails.

For both these aspects each rail may comprise at least one marker. There may be a plurality of equally spaced markers in each rail. The markers may be solid or hollow. The markers may be circular. There may be three rails comprising a top rail, a centre rail, and a bottom rail.

The printed encoding may be by using at least one of Short Term Fourier Transform and Code Excitation Linear Prediction. Alternatively or additionally, the encoding may be by use of the Short Term Fourier Transform to produce a plurality frames, every other frame being deleted prior to printing.

Laterally aligned markers in each of the plurality of rails may be able to be used for determining positions of all other markers. The centre rail may have markers encoding digital data. The digital data may comprise an audio tag.

The printed encoding may be by use of greyscale, each dot of the greyscale having at least one white guard bit in a cellular configuration. The cellular configuration may be a 2×2 cell, the dot being in one segment of the 2×2 cell, all other segments being for guard bits. Alternatively, the cellular configuration may be a 1×2 cell, there being no horizontal guard bit.

The audio signal may have removed therefrom frequency in the range 0 to 125 Hz prior to encoding.

The printed encoding may comprise a first portion in which the encoding is in a first direction, and a second portion in which the encoding is in a second direction.

The printable audio format may also be arranged in a plurality of portions with an order for joining of the plurality of portions being contained in header data of each portion.

Crucial audio data may be closer to the centre rail.

Alternatively or additionally, the printable audio format may comprise a central marker and a printed encoding of an audio signal arranged around and concentric with the central marker. The printed encoding of the audio signal may comprise a plurality of radially arranged short term Fourier transformed audio frames arranged in columns with lower frequencies at a radially outer portion of each column, and higher frequencies at a radially inner portion of each column. The audio frames may be for magnitude only.

In a penultimate preferred aspect there is provided a photograph comprising an image, and a printable audio format as described above. The printable audio format may be a part of the image, or in a border around the image. The printable audio format may be on a self-adhesive label for attachment to one of: the photograph, a page of a photograph album containing the photograph, and a photograph frame containing the photograph.

According to a final aspect there is provided a method for luminance smoothing comprising:

determining a luminance of an extracted marker of a printed audio format;

changing a brightness level of a region around the extracted market for more uniform lighting of the printed audio format.

Prior to step (a), a mesh of extracted markers may be formed with the extracted markers comprising vertices of the mesh. Luminance may be determined by interpolation from the extracted markers.

BRIEF DESCRIPTION OF THE DRAWINGS

In order that the invention may be fully understood and readily put into practical effect, there shall now be described by way of non-limitative example only preferred embodiments of the present invention, the description being with reference to the accompanying illustrative drawings, in which.

DETAILED DESCRIPTION OF PREFERRED EMBODIMENTS

Figure 1:
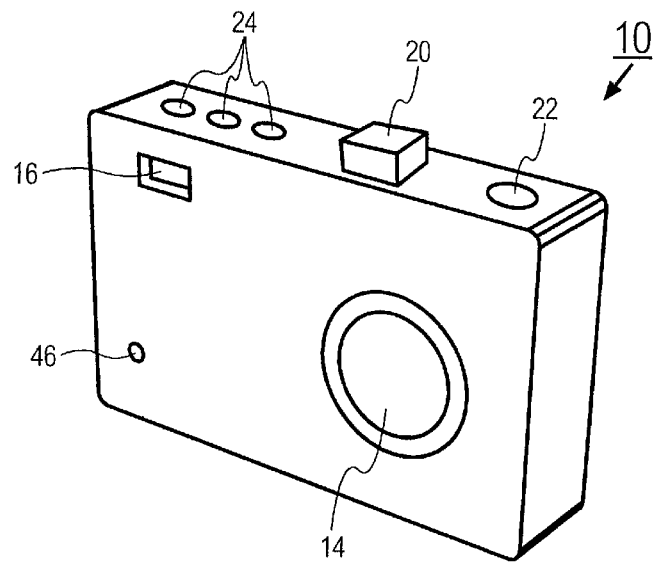
FIG. 1 is in a front perspective view of a first embodiment.
Figure 2:
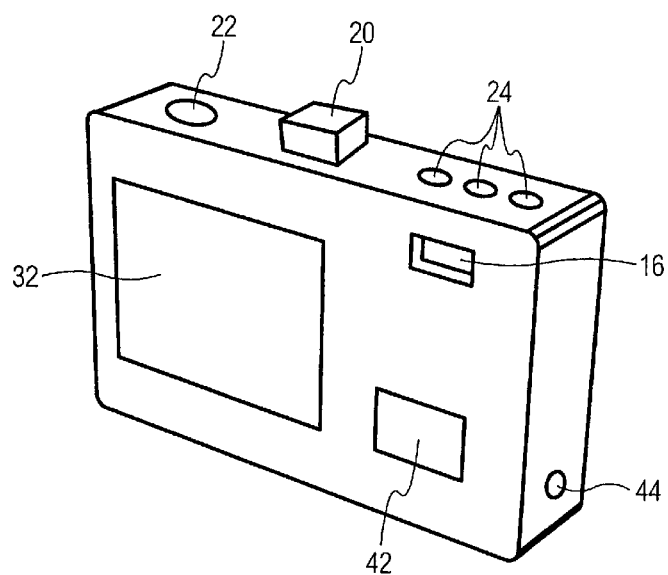
FIG. 2 is a rear perspective view of the first embodiment.
Figure 3:
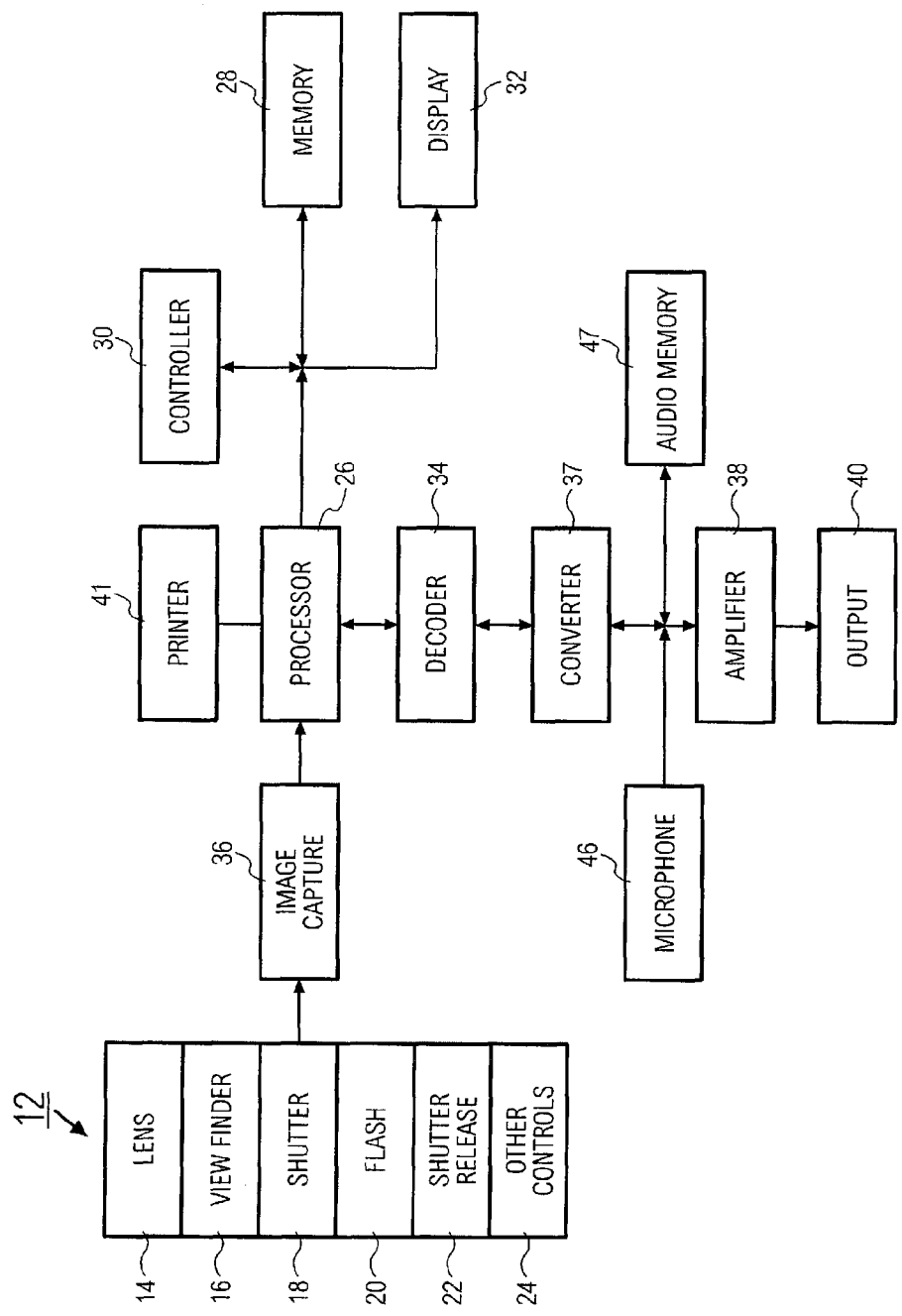
FIG. 3 is a block diagram of the embodiment of FIG. 1.

To refer to FIGS. 1 to 3 there is shown a digital still camera 10. Although a simple form of digital still camera is shown, the present invention is applicable to all forms of digital still cameras including single lens reflex cameras, and digital motion picture cameras in still camera mode, digital camera—enabled mobile telephones, and digital camera-enabled personal digital assistants, and the term "digital camera" is to be interpreted accordingly.

The camera 10 has an imaging system generally indicated as 12 and comprising a lens 14, view finder 16, shutter 18, built-in flash 20, shutter release 22, and other controls 24. Within the camera 10 is an image capturing device 36 such as, for example, a charge-coupled device; and a processor 26 for processing the image data received in a known manner, memory 28 for storing each image as image data, and a controller 30 for controlling data sent for display on display 32. Processor 26 performs conventional digital photographic image processing such as, for example, compressing and formatting a captured photographic image. The imaging system 12, including the image capturing device 36, is able to take and capture photographic images of every day scenes. The imaging system 12 may have a fixed or variable focus, zoom, and other functions found in digital still cameras.

Figure 4:
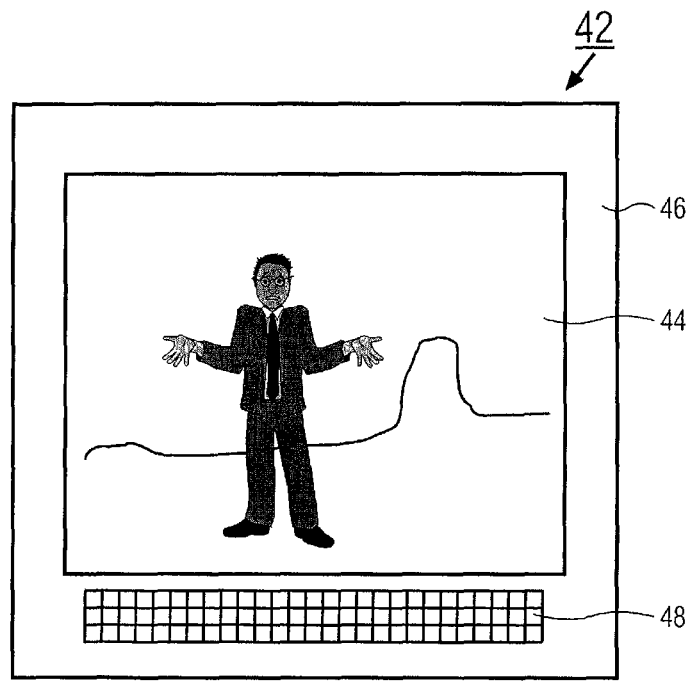
FIG. 4 is a front view of a photograph with a printed audio format.
Figure 5:
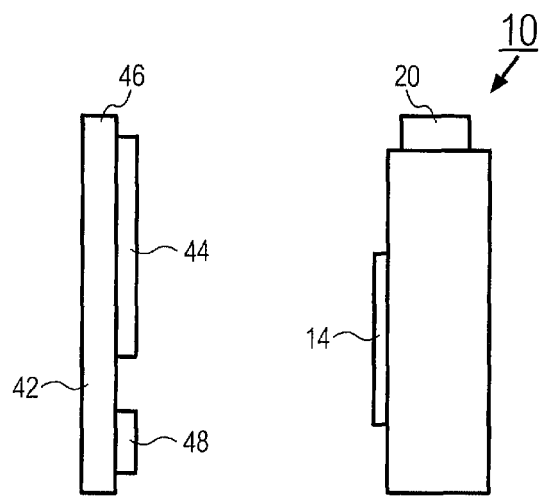
FIG. 5 is side view of the first embodiment as used to capture the printed audio format.

Camera 10 is able to be used to capture, extract and reproduce audio from a printed audio format 48 (FIG. 4). The camera 10 is directed towards the printed audio format 48 in a manner described below, and the imaging system 12 is used to capture an image of the printed audio format 48. Processor 26 extracts encoded audio data from the printed audio format 48 and passes the encoded audio data to a decoder 34 for decoding the audio data. The decoder 34 receives and decodes the encoded audio data to give audio data.

The decoder 34 sends the decoded audio to an amplifier 38 for the amplification of the analog audio to enable it to be output through a sound reproduction device 40. The amplifier 38 may incorporate a digital-to-analog converter in the normal manner to convert the digital audio for reproduction, or it may be part of a converter 37, as shown.

Processor 26 may be separate to or integral with the decoder 34 and/or the amplifier 38. Sound reproduction device 40 may be a loudspeaker 42 and/or a jack 44 for an earphone/headphone set.

In addition, digital still camera 10 may have a built-in microphone 46 to enable camera 10 to capture and store audio at the same time as, or about the time of, taking a photograph. The audio may be stored in a database in storage 47 for subsequent processing, and possible subsequent reproduction. When stored in storage 47, an audio tag is attached to the audio as an identifier to enable the audio to be found when and as required. Microphone 46 output is encoded in codec 34, and then sent for printing. Printing maybe by a printer 41 built in camera 10, or a separate printer. When printed, the encoded audio is a printed audio format. Microphone 46 output may be converted from analog to digital in an analog-to-digital converter. This may be part of the converter 37, making converter 37 a digital-to-analog and analog-to-digital converter.

Preferably lens 14 of camera 10 is able to focus at a relatively close distance such as, for example, 4 cm. To facilitate this, one of the controls 24 may be for a macro setting, or may be for a special setting for capturing the image of the printed audio format 48.

As shown in FIG. 4 there is document, printed photograph or other image-carrying printed object 42 having an image 44 or other data thereon. The image 44 may occupy all of one surface of photograph 42 or, preferably, has a peripheral border 46. Located on photograph 42, and preferably in border 46, is the printed audio format 48 containing encoded audio. The printed audio format 48 may be on the rear of photograph 42, if required or desired.

Figure 6:
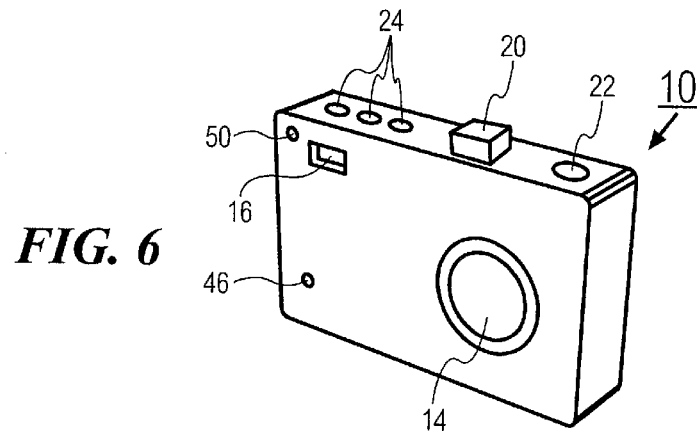
FIG. 6 is a front view of a second embodiment.

To have the lens 14 at the correct distance from printed audio format 48, there may be used an attachment, or built-in facilities, to assist. These are illustrated in FIGS. 6 to 10. FIG. 6 shows the use of a single light source 50 built into the camera 10. Alternatively, it may be separate to the camera 10 but releasably attachable to the camera 10. The light source 50 may be a narrow-angle LED or a low power laser that is directed or aimed at the photograph 42, and in particular at a prescribed location on, or adjacent to, the printed audio format 48 such as, for example, either end, the centre, and so forth. The camera 10 may be moved towards and away from the printed audio format 48. The processor 26 may continuously evaluate an input video stream received through lens 14 for a valid printed audio format 48. This has problems of additional computational requirement for continuous evaluation, uncontrolled lighting, and the introduction of perspective distortion if the lens 14 is not parallel with the printed audio format 48.

Figure 7:
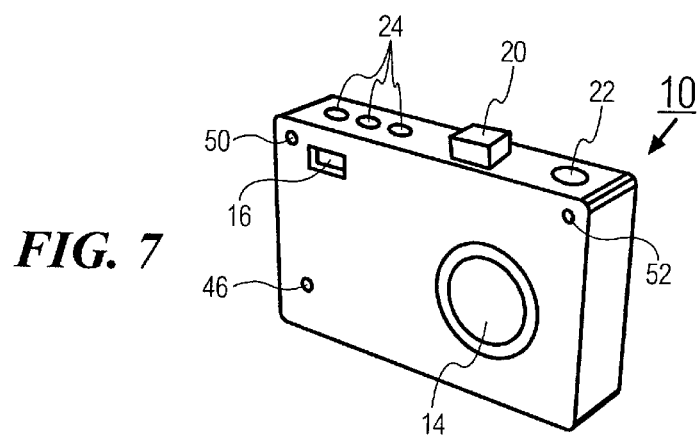
FIG. 7 is a front view of a third embodiment.

To address the issue of continuous evaluation, the embodiment of FIG. 7 may be used. Here, there is a second light source 52 spaced apart from first light source 50. Again, both light sources 50, 52 or either light source 50, 52 may be built-in to camera 10 (as shown) or may be separate from, or releasably attachable to, camera 10. The light sources 50, 52 are focused so that their beams cross when the lens 14 is the prescribed distance from the printed audio format 48. In this way processor 26 needs to process printed audio format 48 once.

Figure 8:
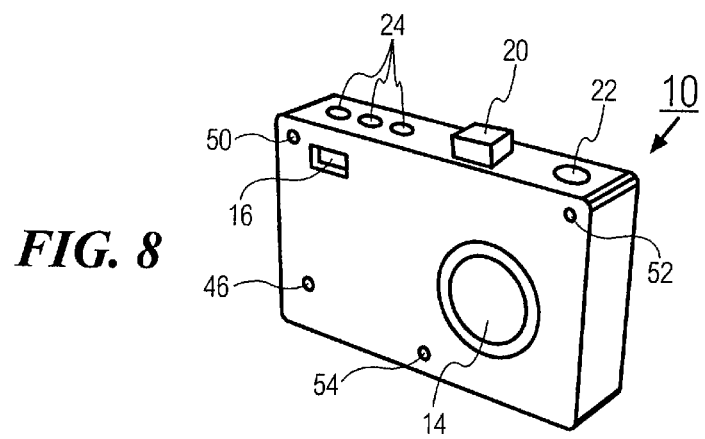
FIG. 8 is a front view of a fourth embodiment.

To address the issue of perspective distortion, the embodiment of FIG. 8 may be used. This is the same as FIG. 7 except that a third light source 54 is also used. Light source 54 is spaced from light sources 50, 52. When the beams of the three light sources 50, 52 and 54 focus on the one point, the lens 14 is the correct distance from and is parallel to the printed audio format 48. Light source 54 may also be built-in to camera 10 (as shown) or may be separate from and releasably attachable to camera 10. Alternatively, the three light sources 50, 52, 54 may be mounted on a single frame (not shown) attachable to camera 10. Such a frame may also contain a power source for the light sources 50, 52, 54.

Figure 26:
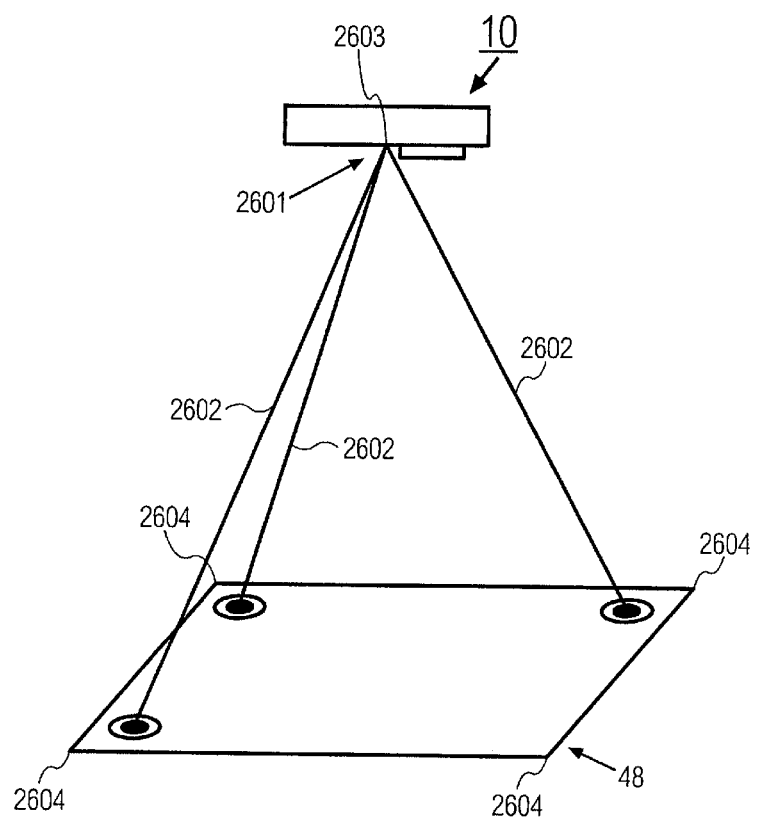
FIG. 26 is an illustration of an eighth embodiment.

As shown in FIG. 26, and further alternatively, there may be two or three light sources at the one location 2601 in camera 10. Each light source has a beam 2602, with the individual beams diverging from each other. For three light sources the beams 2602 will form the apexes of a triangle on the printed audio format 48. Rather than two or three light sources there may be the one light source 2603 with one or more lenses to form the two or three divergent beams 2602. The divergent beams 2602 are to locate on or adjacent corners 2604 of the printed audio format 48 when the camera 10 is at the correct distance from and parallel to the printed audio format 48.

Figure 9:
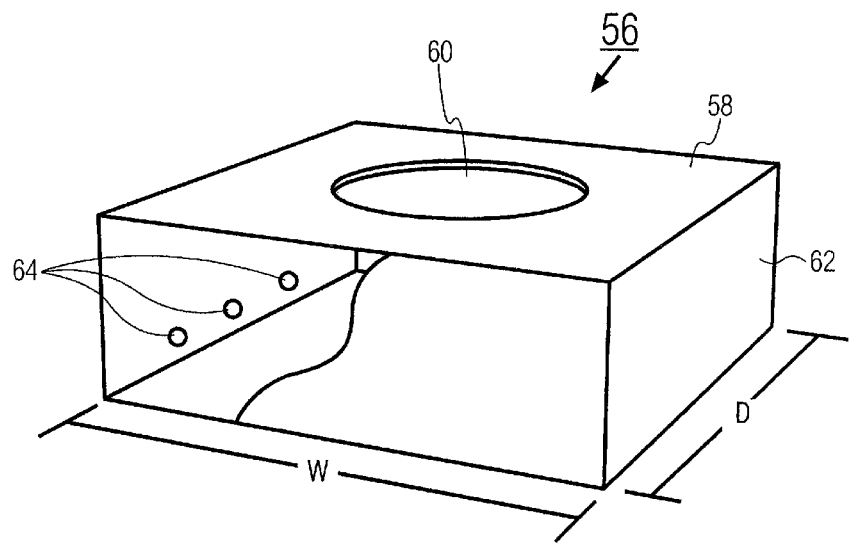
FIG. 9 is a front view of a fifth embodiment.

A further embodiment is shown in FIG. 9. Here there is shown an attachment 56 to be placed over and/or around lens 14 and to be placed on photograph 42 such that lens 14 is directly over, parallel to, and correctly spaced from printed audio format 48.

The attachment 56 comprises a top 58 with a central opening 60 shaped and sized to allow lens 14 to pass therethrough (if lens 14 projects from camera 10) or to operate therethrough. Either way, opening 60 is sized and shaped to allow lens 14 to be able to capture the image of printed audio format 48. Depending from top 58 are at least two opposed sides 62 of the required height to have lens 14 the correct distance from printed audio format 48. The sides 62 may be made of any suitable material and may be solid, transparent, translucent, or opaque. Preferably there are four mutually perpendicular sides 62.

If desired, the attachment 56 may include one or more light sources 64 mounted in one or more of the sides 62 to provide control over the illumination of the printed audio format 48. The light sources 64 may be LEDs and may be separately powered, or may be powered by the camera 10 battery. To minimise reflection from glossy or like surfaces, the light sources 64 are preferably diffused by a diffuser, or placed as low as possible in sides 62 so they are outside the visible region of lens 14. To assist this, the attachment 56 may be wider than the printed audio format 48 is long. Thus the sides 62 may be of different widths. Preferably, the internal dimensions of the attachment 56 (width W and depth D) are slightly greater than the corresponding dimensions of the printed audio format 48.

In capturing an image of the printed audio format 48 it is likely that more than just the printed audio format 48 will be captured. Some of the material of photograph 42 surrounding the printed audio format 48 may also be captured. In that case, once the image is captured, processor 26 will either extract the encoded audio data from the entire image, discard the non-printed audio format data that has been captured and then extract the encoded audio data, or will extract the data relating to the printed audio format from the captured image and then extract the encoded audio data from the data of the printed audio format.

Figure 10:
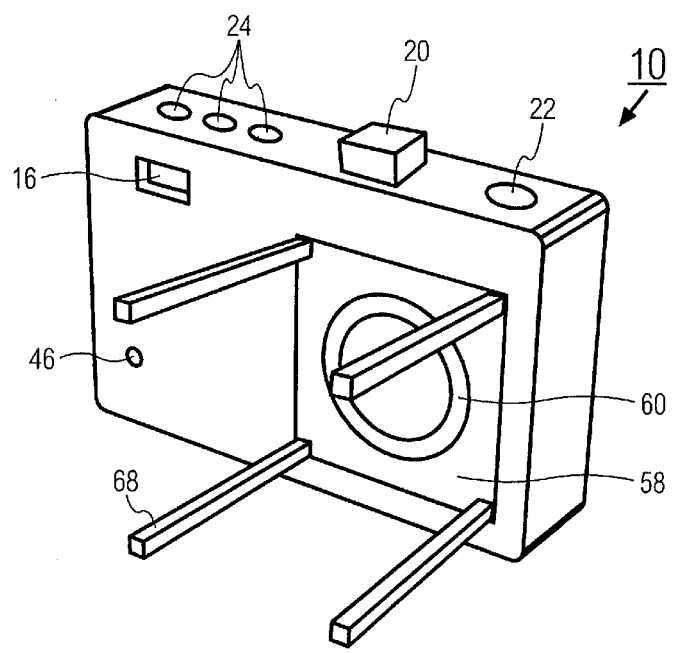
FIG. 10 is a front view of a sixth embodiment.

An alternative form is shown in FIG. 10 where sides 62 are replaced by four corner legs 68. Each leg 68 is located where there would have been a junction of sides 64. The height and spacing of legs 68 is preferably the same as for sides 62.

Figure 11:
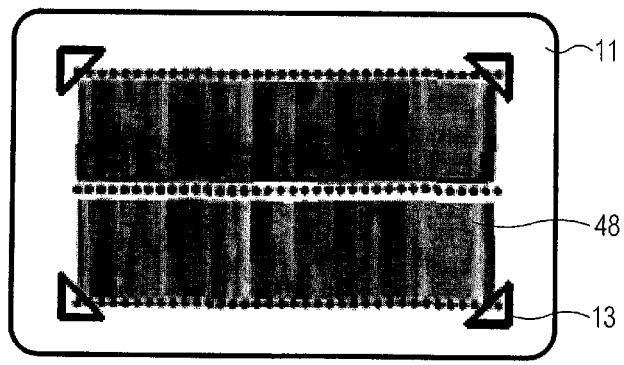
FIG. 11 is a view of a seventh embodiment.

FIG. 11 shows a further embodiment. Here there is no change to the camera 10 other than what is in the view finder 16 frame 11. The view finder 16 frame 11 is shown having the printed audio format 48 in view. By having frame guides 13 forming part of the frame 11, when the corners of the printed audio format 48 are overlaid by the frame guides 13 the printed audio format 48 is substantially correctly framed, thus reducing perspective distortion and assisting in capturing the data in the printed audio format 48 with reasonable accuracy. At least two frame guides 13 are required—one for each end of printed audio format 48, preferably diagonally opposite of printed audio format 48. However, four frame guides 13 are preferred, as is shown. The view finder 16 may be optical or may be electronic, as in an LCD display, or the like.

If desired, and if the camera 10 has a frame guides macro function 13 may only appear in the frame 11 when the camera 10 is in the macro mode.

Figure 12:
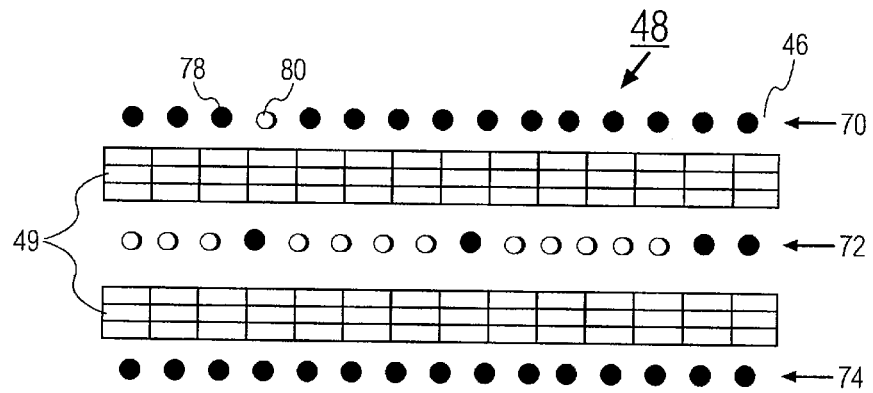
FIG. 12 is a front view of a preferred form of printed audio format.
Figure 13:
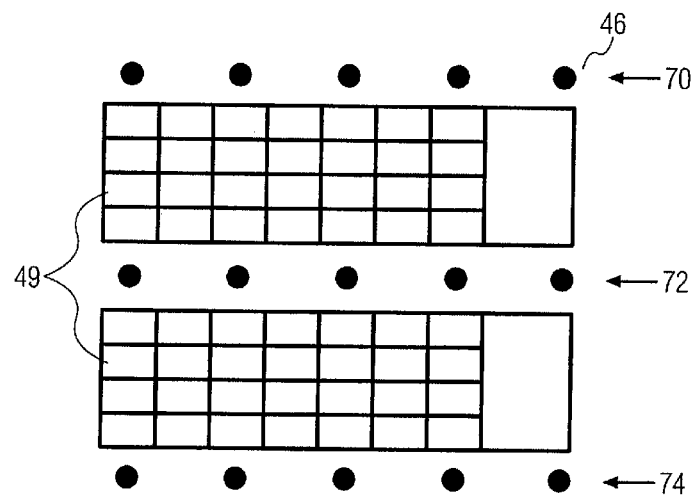
FIG. 13 is an enlarged view of part of the printed audio format of FIG. 11; fourth embodiment.
Figure 14:
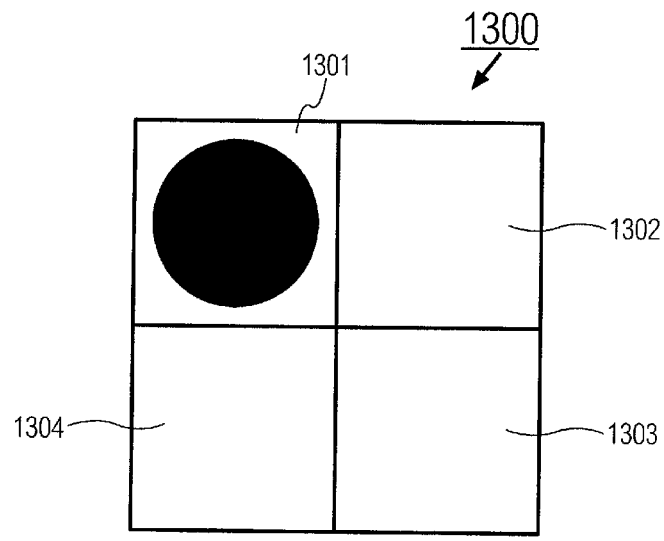
FIG. 14 is an illustration of a first form of cell configuration.
Figure 15:
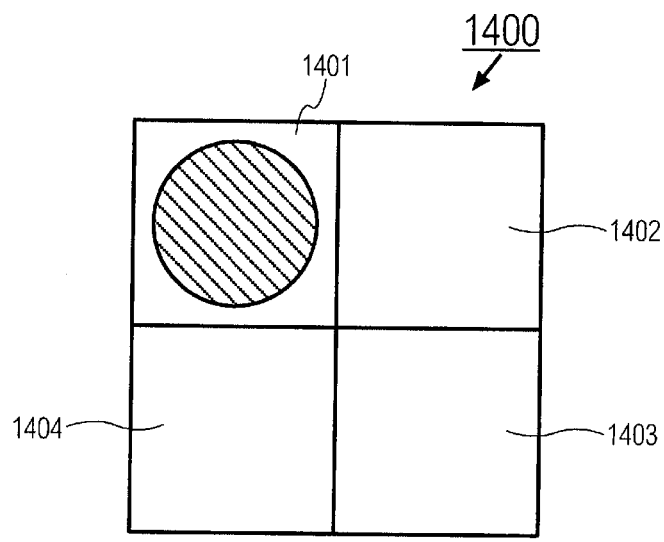
FIG. 15 is an illustration of a second form of cell configuration.

FIGS. 12 to 14 show a preferred form of the printed audio format 48. The printed audio format 48 may be encoded and decoded using a short term Fourier transform ("STFT") codec and/or a Code Excitation Linear Prediction ("CELP") codec. An STFT codec uses continuous grey tone, whereas a CELP codec uses black and white.

The printed audio format 48 is a printout containing audio content 49, and various markers to assist extraction by the camera 10. The markers are arranged in a plurality of rails, preferably three rails—a top rail 70, a centre rail 72, and a lower rail 74. There may be any number of rails from one up including, for example, 1, 2, 3, 4, 5, and so forth. The audio content 49 is centred around the centre rail and between the rails irrespective of the number of rails. The rails are generally parallel, and are equally spaced. As shown, with the three rails 70, 72, 74 the audio content 49 is located in two zones—one between top rail 70 and centre rail 72, and the other zone between centre rail 72 and bottom rail 74.

The rails 70, 72, 74 are preferably:
resistant to channel error;
rotational invariant;
able to survive partial crop;
audio CODEC independent, so that the same rail works with either CELP or STFT;
fit inside a 1"×1" area at 360 dpi;
able to facilitate fast marker extraction;
able to embed the stored audio tag; and
flexible and extensible.

Stored audio is the captured audio stored digitally, and possibly permanently, in the camera audio database. The stored audio may be compressed using CELP or other suitable standard compression such as, for example, ADPCM. Each storage of an audio clip has a unique tag number. When a stored audio is encoded into a printed audio format, the audio tag is encoded in the header of the printed audio format. During decoding, and after locating the center rail, the header is decoded first, and the stored audio tag extracted. Based on the extracted tag, the processor may find the stored audio in the database. If found, it will proceed to play back the stored audio. If not found in the database, it will proceed to decode the printed audio.

In this way, if the same camera, or the same camera storage device containing the audio database (e.g. Flash card, memory stick, or the like) is used to capture as well as playback the audio, if the audio is still stored in the database, it can be found by the audio tag, extracted from the database, and replayed directly from the database, thereby eliminating the decoding step.

Each rail 70, 72, 74 comprises a plurality of equally spaced and vertically aligned markers 76. The markers 76 are preferably circular, as shown, although they may be of other shapes such as for example, square, octagonal, elliptical, and so forth. They may be solid 78 or hollow 80. The markers 76 are preferably rotationally invariant to enable fast circle detection. The markers double as data storage, by using either a solid 78 or hollow 80 markers to encode data bits.

The size of the markers 76 and the inter-marker distance is fixed. By doing so, only two markers are needed to determine the positions of other markers, thereby easing marker detection. A third marker may be used to validate the two markers. The data area height can vary, and such variation is preferably encoded in the centre rail 72.

Figure 20A:
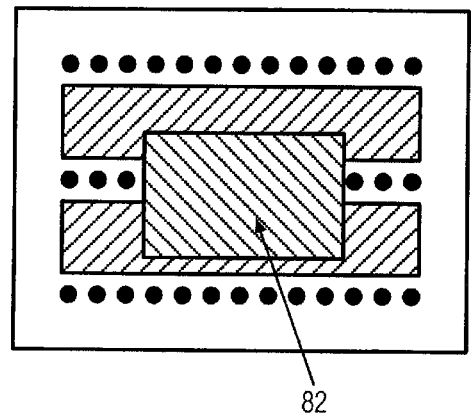
FIGS. 20A-20C are three illustrations of centre marker searching.
Figure 20B:
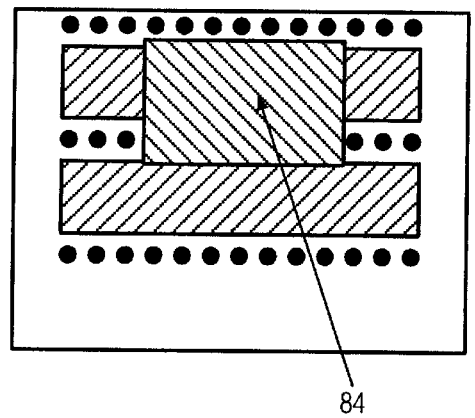
Figure 20C:
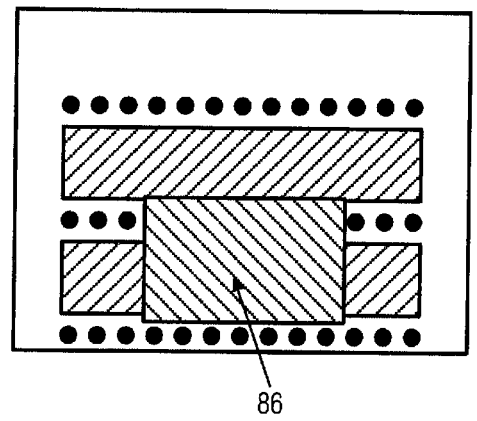
Figure 21A:
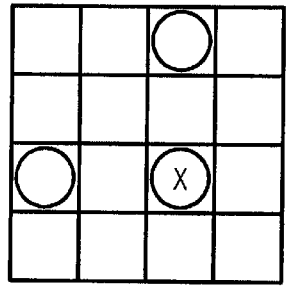
FIGS. 21A-21D are illustrations of four examples of refining threshold.
Figure 21B:
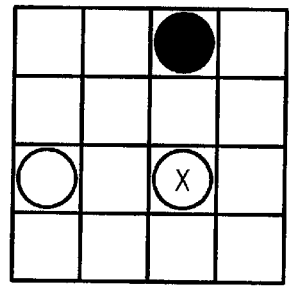
Figure 21C:
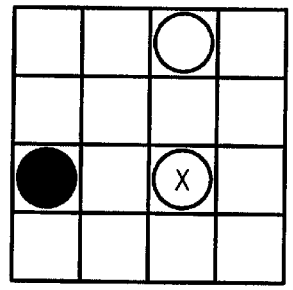
Figure 21D:
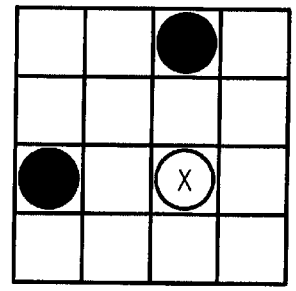
Figure 22:
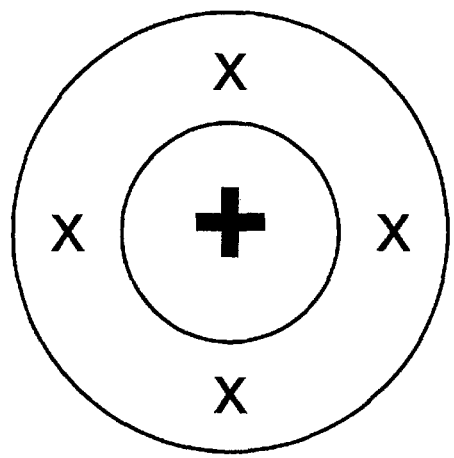
FIG. 22, is an illustration of sample positions for testing if the marker is solid or hollow.

Detection of markers 76 is shown in FIG. 20 and begins by searching for three markers in centre rail 72 in centre region 82—FIG. 20(*a*). The markers are validated. If the markers are found to be not valid, the search continues in other regions as described below. With the location of the three markers, the position of the rest of the markers is predicted. A block-matching search is then performed to refine the predicted position. The predicted position is important as it reduces the search time, and increases its reliability.

If the search for the three markers in the pre-defined centre region 82 fails, searching continues in an upper region 84—FIG. 20(*b*). If that also fails, searching continues in bottom region 86—FIG. 20(*c*). If all three fail, it is assumed that the printed audio format 48 lies in the ideal position and a blind decode is performed. A blind decode assumes that the centre rail 72 is at the exact centre of the captured image.

Given three centre marker positions p0, p1, p2, where p0 is to the left of p1 and p1 to the left of p2, the next predicted left marker's position, pLeftPredicted=p0+(p0−p1). That position is then refined by performing the block match, pLeft=BlockMatch(pLeftPredicted).

The new position is then used to predict the marker to its left. The search terminates when no more markers 76 can be found. A similar technique is then used to search for markers 76 to the right of the three markers.

All markers in centre rail 72 are sorted from left to right. Given the centre rail 72, it is possible to predict the markers 76 of the outer rail 70:

1. let the left-most four markers 76 in centre rail 72 be p0, p1, p2, and p3;
2. the direction vector is given by, dir=p3−p0.
   p3 is used instead of p1 and p2, because p3 is further away from p1, and thus correlation error due to an imperfect block match is least magnified.
3. this vector is rotated 90° anti-clockwise, to get dirUp=rotate90(dir);
4. normalize, dirUpN=normalize(dirUp);
5. the leftmost top rail 70 marker 76 has an estimated position:
   p  TopLeftMarkerPredicted=0+dirUpN×DistanceToTopRail;
6. search for the optimal position to arrive at pTopLeftMarker=BlockMatch(pTopLeftMarkerPredicted).
   If pTopLeftMarker is outside the image, the position is not refined; and
7. the next top rail 70 marker 76 can be estimated by using pTopLeftMarker+(dir/3)

These steps are repeated for the bottom rail 74. The only change is the 90° rotation, which is clockwise for the bottom rail 74.

For the centre rail 72, the type of marker 76 is determined, being either solid 78 or hollow 80, to extract the encoded digital data. This is the header. Based on the header, the distance to the outer (top 70 or bottom 74) rails is known. With this information, it is possible to predict where the outer markers may be. This prediction will be fine-tuned by a search if it is inside the image. If the predicted position is out of the image boundary, due to cropping, the predicted position is used for data extraction.

Given a rectangular region R, and a template T, which is a sample image of the marker, a correlation search from left to right, top to bottom, is performed. This may be coupled with a minimum distance clustering by using the heuristics:

```
For x in left to right of region R
    For y in top to bottom of region R
        Correlate template T at location (x,y), to get correlation value c
        If (c reflects a high correlation)
            Get Hamming Distance to previous Marker, d
            If (d < MinDistance)
                Replace a previous marker if c is better
            Else
                Add a new marker.
                Store its location and c
```

MinDistance is the fixed distance between two markers 76, "Correlate" may use sum-of-absolute-difference approximation, commonly implemented in video processor for Block Matching in MPEG Motion Estimation.

Validating the markers 76 in centre rail 72 requires:
1. at least three markers 76;
2. the distance between markers 1,2 and 2,3 should be the same; and
3. the angles between a line with an endpoint at markers 1,2 and a line with an endpoint at markers 2,3 to be the same to ensure they are collinear.

If any of the above fails, the input image is rejected as invalid. This is useful to minimise computation time for a continuous video stream analysis.

Three rails 70, 72, 74 are used but only the centre rail 72 is required for extraction. A missing or partial outer rail 70, 74 degrades quality for STFT encoding, but does not render it impossible to decode. However, CELP encoding requires the accuracy provided by all three rails 70, 72, 74. Outer rails 70, 74 may be used to increase the accuracy. They can also be used for lens distortion correction as centre rail 72 typically lies close to the optical centre of the lens 14, the optical centre having minimum distortion and defocus. Centre rail 72 may also be used to quickly reject an invalid printed audio format 48. Three rails 70, 72, 74 provide more header data capacity compared to a single centre rail 72.

Both the height and length of the printed audio format 48 may vary. The length can vary to provide more bits to the stored audio tag.

The configuration of the printed audio format 48 may be given as

| | | | | |
|---|---|---|---|---|
| Inter-marker Gap, | Mg | | | |
| Top Marker, Diameter, | Md | ○ ○ ○ | | |
| Gap 1, | G1 | | | |
| Top Data, | Dt | XXXXXXXXX | | |
| | | XXXXXXXXX | | |
| | | XXXXXXXXX | | |
| Gap 2, | G2 | | | |
| Centre marker | | ○ ○ ○ | | |
| Gap 3, | G3 | | | |
| Bottom Data, | Db | XXXXXXXXX | | |
| | | XXXXXXXXX | | |
| | | XXXXXXXXX | | |
| Gap 4, | G4 | | | |
| Bottom marker | | ○ ○ ○ | | |

○ = Marker
X = Data

The following attributes are derived from the parameters of the printed audio format 48.

Centre to Top Outer Rail=$Md+G1+G2+Dt$

Centre to Bottom Outer Rail=$Md+G3+G4+Db$

Drain1=ceil($Md/2$)+$G1$

Drain2=−(floor($Md/2$)+$G2$)

Drain3=ceil($Md/2$)+$G3$

Drain4=−(floor($Md/2$)+$G2$)

Centre rail 72 to outer rail 70, 74 is used to predict locations of the outer rails 70, 74. Drain1 to Drain4 are used during data extraction.

The audio tag may be encoded in the centre rail 72 using solid 78 and hollow 80 markers, representing "0" and "1" respectively. The two types of marker 78, 80 are differentiated by comparing the centre of the marker with the neighbouring colours. The difference is noted and tested with a threshold value to decide if it's a hollow 80 or solid 78 marker. The use of differences gives better tolerance to lighting variances as is illustrated in FIG. 21 where:

+ is the centre of the marker; and
x is a neighbouring pixel. "x" that lies in the middle of the hollow marker rim. e.g. if the marker has a diameter of 7 (radius=3.5) the distance will be roughly 2.

Parsing is from left to right, so that the least significant bit is on the left and side.

This allows the length of the last field, Audio Tag, to vary with the length of the printed audio format 48.

One configuration may be:

| Bit Location | Description |
|---|---|
| 0 | Reserved, always 1 |
| 1 | Reserved, always 0 |
| 2 | First stamp indicator |
| | 0- Additional stamp |
| | 1- First stamp |
| 3, 4 | Encoding Type (e.g. STFT or CELP) |
| 5 | Cell configuration |
| | 0- 1 × 2 |
| | 1- 2 × 2 |
| 6-8 | Index of Additional Printed Audio |
| | (for multiple Printed Audio) |
| | For first Printed Audio, it is the |
| | number of Additional Printed Audio. |
| 9-31 | Stored Audio Tag |
| 32 | Last bit set to 0, which is opposite of |
| | bit 0, to detect upside down stamp. |

As shown in FIG. 14, the bits are preferably printed in a 2×2 cell 1300 with three guard bits as follows:

| | |
|---|---|
| Bit (1301) | Guard (1302) |
| Guard (1304) | Guard (1303) |

A bit may be black or white to represent "1" or "0" respectively, or may be continuous grey tone. The guard bits are white spaces and are to allow for dot gain. Using a cell without guard bits may result in an increase in bit error. The data area 49 may have 82 cells per column, and 5 columns per segment. Data flows from left to right, top to bottom.

Due to paper absorption and imperfect printing, a black dot spreads beyond its boundary. This is countered by using the guard bits (1302, 1303, 1304) in the 2×2 cell configuration 1300. The guard bits assume that the spread is less than one pixel, resulting in a clear printout. However, due to, for example, lens imperfection during capturing, a further degradation may occur which may further smudge the print.

A dot from an inkjet printer spreads beyond its pixel boundary causing dot gain. The ability of paper to absorb and restrain its spread to neighbouring area is critical to minimise dot gain. A 300 dpi droplet is worth only 150 dpi if it spreads into one surrounding pixel; and worth only 75 dpi if it expands into two surrounding pixels. For example, if two black dots are printed and leave a white dot between them, the dots gain cause the white dot to appear as grey or, in many cases, black. Coated paper resists absorption, while uncoated paper allows a greater absorption, and thus shows more gain. Other factors affecting dot gain are ink viscosity, rimming, and mechanical imperfection. These are not controlled to allow for variation. This is able to accommodate various printers. What can be controlled is where the dots are placed to minimise interference, and the type of ink and paper used.

Dot gain may make a printout appear darker, increasing decoder error. A standard practice is to compensate for dot gain by "brightening" the source image using gamma correction or calibrated correction. Gamma correction has the advantage of preserving the dynamic range. The disadvantage is that the gain is non-linear, which may cause distortion if used excessively. Dot gain control may be enhanced empirically by performing an additional gamma correction before combining or compositing it with the image. In such a case, the additional gamma correction only affects the printed audio format 48, leaving the image 44 untouched. The printer driver can then perform its standard gamma correction over the entire document 42.

Horizontal dot gain may be more than vertical dot gain. This may be due to the print head moving horizontally so the dots travel with a horizontal velocity before impacting the paper, causing horizontal smear. By capitalising on the small vertical dot gain, the vertical guard bit may be removed and a 1×2 cell used.

CELP encodes 16 bits 8 Khz speech into a 4800 bps stream in 30 ms frames. Each CELP frame has 144 bits, or 18 bytes. A Reed Solomon Forward Error Correction code may be appended to a block of CELP frames:

A CELP Block consists of 25 columns of 82 cells, giving a total of 82 *25 bits=256.25 bytes;
each block uses only 255 bytes, leaving 10 bits unused;
fit 12 CELP frames per block, taking up 12 *18=216 bytes; and
Reed Solomon code takes up the remaining 39 bytes.
The characteristic of a CELP printed audio format is:
Each printed audio format is self-contained;
The size of the printed audio format is about 1"×0.5" for audio duration of 2.5 seconds;
Each block can be individually decoded and tolerates 19 single byte errors;
A block is an autonomous data unit;
82 cells per column;
Printed audio format capacity=14, 350 bits or approximately 1.8 KB with 175 columns of 82 cells.
Effective capacity, deducting error correction code, is approximately 1.5 KB.

The error tolerance rate refers to a single block. However, based on channel error, certain blocks at the edge of the image, away from the optical centre, are more prone to error than those in the middle. Higher error tolerance for such high-risk blocks may be used, but this decreases capacity. An alternative is to interleave the data across the printed audio format 48. The advantage of interleaving is that capacity remains the same. The disadvantage is that the entire printed audio format 48 must be extracted before decoding can begin. If one side of the printed audio format is missing from the image, the entire printed audio format may be unusable. Interleaving a few blocks instead of the entire printed audio format 48 may provide a better solution.

In STFT encoding an 8-bit 8000 Hz speech is first converted to STFT using the parameters.

256 window size;
Hanning windowing function;
128 hop size

The data is then converted to magnitude and phase, resulting in 128 magnitudes and 128 phases per frame. The 128 magnitudes are encoded and the 128 phases are discarded. In the co-pending PCT and USA utility applications filed contemporaneously herewith based on and claiming the priority of our U.S. provisional application No. 60/531,029 filed 19 Dec. 2003 and entitled "Method and System to Process a Digital Image" (the contents of which are hereby incorporated by reference) there is disclosed a method for providing an efficient and error-tolerant process for reconstructing the phases during decoding.

The 128 8-bit values are encoded using a single column so that each column contains one complete frame. As is stated above, the cell configuration is 2×2 with one data bit and three guard bits, which is the same as the configuration of CELP. Unlike the digital CELP, data is rendered in continuous grey tone instead of black or white. Colour may be inverted so that 255 becomes pure black, and 0 becomes white.

To increase error tolerance, the STFT bands may be divided into three groups, and more important lower frequency bands may be placed closer to the centre rail 72. For an 82 cells per column of STFT, bands 32 to 72 may be from centre rail 72 to bottom rail 74; and bands 0 to 31 then bands 72 to 81 from centre rail 72 to top rail 70. The concept can be extended for 128 cells per column.

If 128 cells per column were used the size would increase. To reduce the size, 82 cells are encoded to make it the same size as if CELP were used. Keeping only 82 out 128 bands means the frequency range is only up to 2.6 kHz, instead of 4 kHz.

The frequency range may be increased by discarding the first four bands (0 to 125 Hz), since small loudspeakers cannot reproduce them. Every other band from the 48th band onward is encoded as the power in the higher frequencies is more likely to be weaker than in the lower frequencies. This effectively increases the frequency range to about 3.7 kHz. During decoding, the missing bands are linearly interpolated from their surrounding bands. The first four bands and the last few bands remain zero.

A colour inkjet printer can only print solid colour. In most cases, these colours are cyan, magenta, yellow, and black (CMYK). When printing a grey "dot", tiny black dots are printed in a specific pattern, in a process known as half toning to simulate a shade of grey. Human eyes see grey instead of individual dots because the dots are too small to be discerned as human eyes have a resolution power of 1 arc-minute. Anything smaller than one arc minute is averaged. A scanner, however, may discern beyond 1 arc-minute, and may actually see the dots instead of grey.

The process of deriving a grey value given a halftone image is inverse halftoning. The low pass nature of camera lens 14 may be used to perform the "averaging". Additional averaging may be performed by area sampling during the extraction process. Because of halftoning and the use of grey colours, analog grey tone encoding may require a higher resolution printer.

A camera lens warps the geometry of an image resulting in barrel and pincushion distortion. The "resolution" of a lens degrades and becomes defocused away from its centre. Lens distortion correction may be performed to rectify this. By placing crucial data nearer to the centre rail 72, this problem may be further reduced.

Exposure time affects analog (greyscale) data as it determines not only the "gain" but also the ability to resolve different shades of grey. An improper exposure time may lead to overexposure or under-exposure of the image and may compress the grey scale, leading to inferior data extraction, especially for analog encoding Improper exposure may result in the audio sounding "thin" due to over-exposure, or to have excessive "echo" and "distortion" due to under-exposure. Using an illuminated opaque cap covering the printed audio format 48 may assist to overcome this problem.

Extracting the audio data from the printed audio format 48 linearly interpolate the positions of cells from the positions of markers 76.

For digital extraction, the thresholding process is done dynamically. Extraction begins by bi-linearly sampling all the cells of a segment, and the average value is used as a threshold to convert the greyscale into binary. A segment is enclosed by four adjacent markers 76 in a rectangular configuration. This approach assumes that the "0" and "1" bits are equally distributed. This works better than a fixed threshold, especially under uneven lighting. Using the entire printed audio format 48 instead of just a segment to derive the average may result in a more equal distribution of "0" and "1", but assumes that illumination is constant for the entire image, which is quite likely to be false. The minimum and maximum extracted values are also stored for refining thresholds.

A white dot is darker if neighbouring dots are black. As scanning proceeds from left to right, top to bottom, the threshold is adjusted if the top or left dot is black, resulting in improved accuracy, especially at the out of focus region near the edges of the printed audio format. Similarly, the threshold is adjusted when the surrounding pixel is white. The adjustment is illustrated in FIG. 21 and is as follows:

Left and top pixel white: new threshold=0.1*Max+ 0.9*Threshold (FIG. 21(*a*))

Top pixel black: new threshold=0.1*Min+0.9*Threshold (FIG. 21(*b*))

Left pixel black: new threshold=0.1*Min+0.9*Threshold (FIG. 21(*c*))

Left and top pixel black: new threshold=0.18*Min+ 0.82*Threshold (FIG. 21(*d*))

The weights are decided empirically.

For analog (greyscale) extraction the average of nine pixels is taken: one centre pixels and eight surrounding pixels each offset by half a pixel, to obtain a more stable grey value. A bias weight favouring the centre pixel maybe used to increase its accuracy. The grey value is then inverted and stored for decoding.

Figure 16:
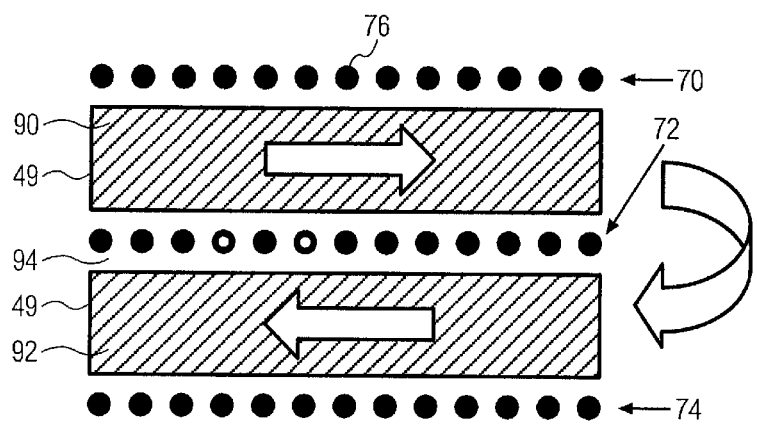
FIG. 16 is an illustration of a second form of printed audio format.
Figure 17:
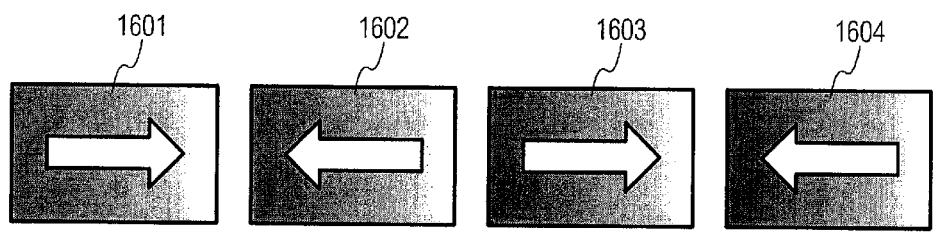
FIG. 17 is an illustration of a third form of printed audio format.

To increase the audio duration is illustrated in FIGS. 16 and 17.

As shown in FIG. 16, the printed audio format 48 may be separated into two along the centre rail 72. The top half 90 encodes the first time period of audio, while the bottom half 92 encodes the second time period of audio either with reduced bands or with smaller cell. To prevent a break being heard, due to uneven lighting, at the join 94 between the top 90 and bottom 92 the bottom half 92 may be encoded in reverse order so that the joining part 94 is on the same end of both halves 90, 92.

Additionally or alternatively, a 2× timescale may be performed by dropping every other STFT frame. Extraction performs an "inverse" timescaling by performing a 0.5× timescale to slow it down. Also, horizontal compression may be used by using a 1×2 cell where two guard bits are deleted to give the structure Bit3

Guard

Thereby halving the space required for each bit.

FIG. 17 illustrates where multiple printed audio are used. Here, there are four printed audio 1601, 1602, 1603 and 1604. Their images are preferably captured at the one time. Alternatively, they may be captured separately as required or desired. To address uneven lighting within an opaque lens attachment, they alternate in their encoding so that the first 1601 is encoded from left to right, and the second 1602 is encoded from right to left. Similarly for the final two, 1603 and 1604. In this way 1601 and 1602 may have their images captured at the one time, and 1603 and 1604 captured subsequently. The processor combines all the data into one, and used the header data to control this task. The audio is replayed all at the one time.

Figure 18:
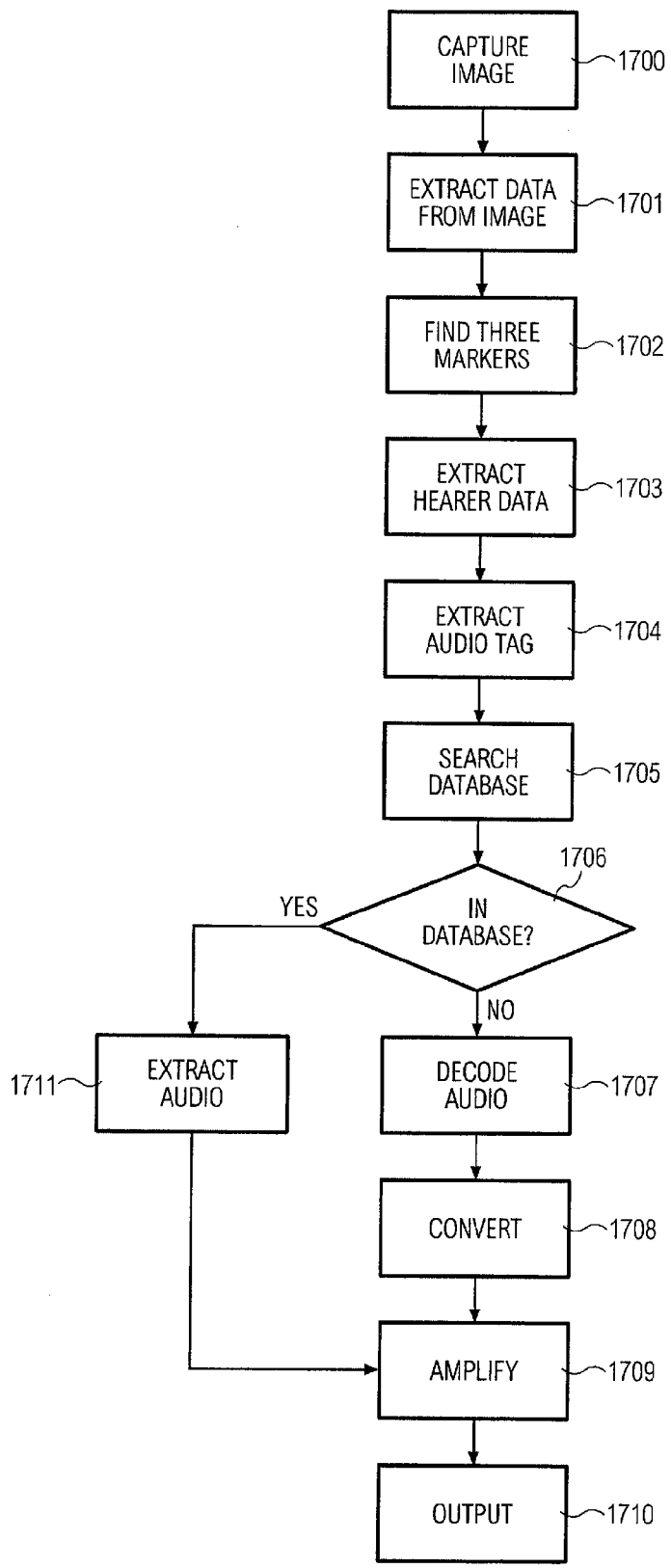
FIG. 18 is a flow chart for the capturing of an image of the printed audio format and replaying the audio.

FIG. 18 shows the overall process for audio reproduction:

the image is captured (1700)

the data of the printed audio format 48 is extracted from the image (1701)

the three centre markers are found by the search (1702)

the header data extracted (1703)

the audio tag extracted (1704)

database is searched for the audio tag (1705)

if the audio tag is in the database (1706), the audio is extracted (1711) then amplified (1709) and reproduced if the audio tag is not in the database (1706) the audio is decoded (1707) and the decoded audio is then either converted (1708) and amplified (1709) or amplified (1709) and converted (1708)

the audio is output (1710)

Figure 19:
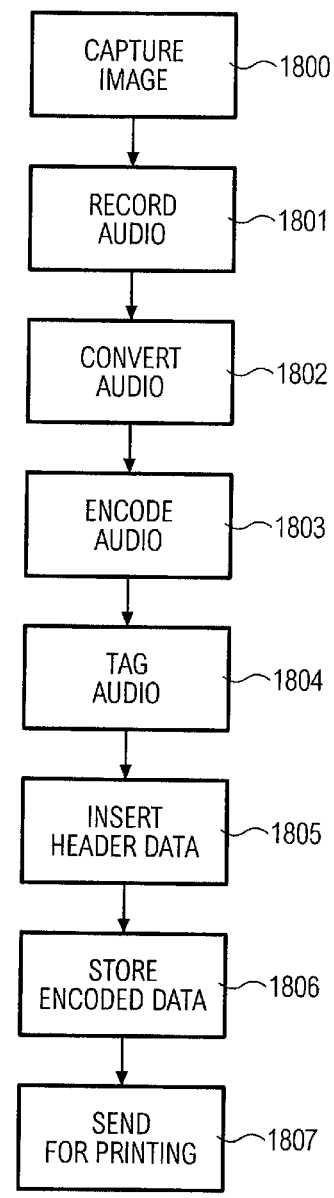
FIG. 19 is a flow chart for the capturing of audio and creation of a printed audio format.

FIG. 19 shows the process for encoding audio:

the image is captured (1800)

the audio is recorded (1801)

the audio is converted (1802)

the audio is encoded (1803)

the audio is tagged (1804)

header data is inserted (1805)

the encoded data stored (1806)

and finally sent for printing (1807).

If the output (1710) is by the camera 10 being used in conjunction with a computer, sound system or the like, for audio reproduction, conversion (1708) and amplification (1709) may be eliminated.

Figure 23A:
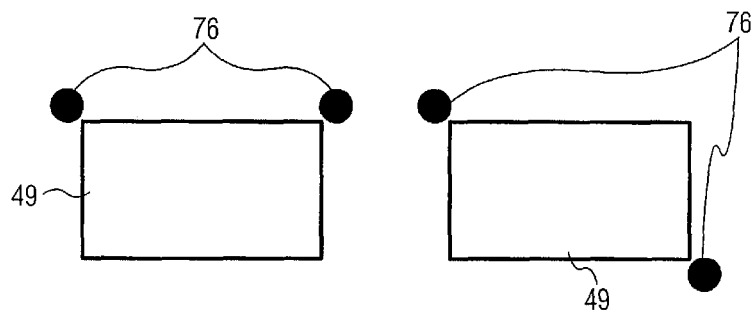
FIGS. 23A and 23B are illustrations of alternative marker configurations.
Figure 23B:
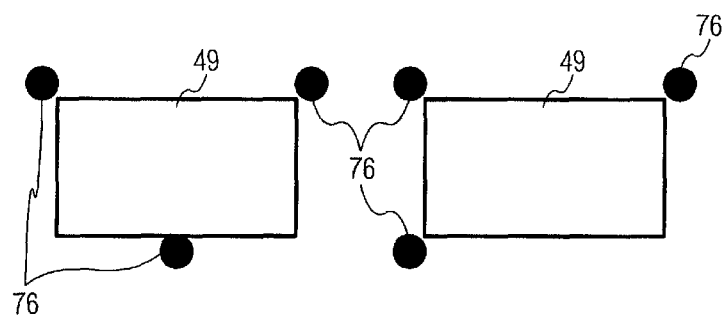

FIG. 23 illustrates two alternative forms of printed audio format 48. FIG. 23(*a*) shows where perspective distortion is not taken into consideration and thus there needs to be only two markers 76 for each audio content 49.

The markers 76 may be arranged at any location around or adjacent the periphery of audio content 49, but are preferably at or adjacent the corners of audio content 49.

If perspective distortion correction is to be included, at least three markers 76 are required for each audio content 49. This is shown in FIG. 23(*b*). Again, the markers 73 are arranged around or adjacent the periphery of each audio content 49 and most are at or adjacent a corner of each audio content 49. However, this is not essential as is shown by marker 76' that is intermediate an edge of a side of an audio content 49.

Figure 24:
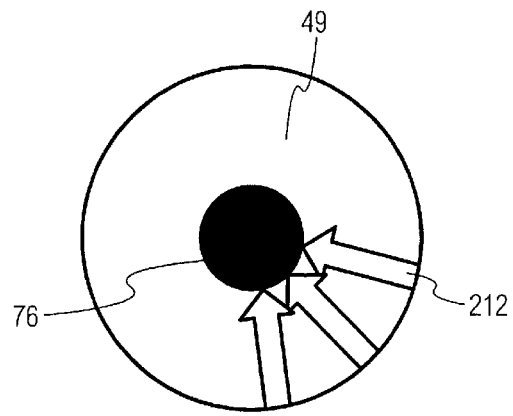
FIG. 24 is an illustration of a radial configuration.

As is shown in FIG. 24, a circular marker printed audio format 210 may be used with a central marker 76 and a single audio content 49 arranged concentrically with marker 76. STFT magnitude frames arranged in columns 212 may be used extending radially of marker 76 with low frequency bands being at the outer periphery and extending to high frequency bands adjacent marker 76.

Figure 25:
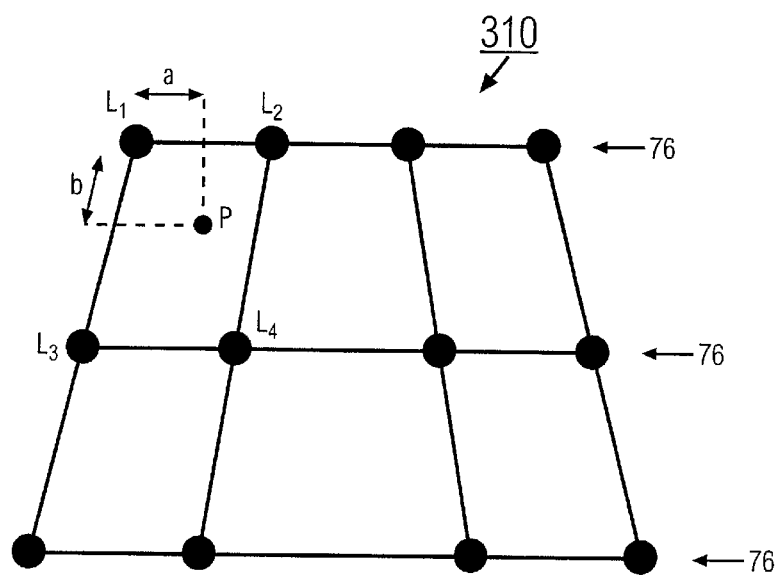
FIG. 25 is an illustration of luminance smoothing.

Luminance smoothing is shown in FIG. 25. Here, the luminance of each extracted marker 76 is used to predict the brightness of the region around it. By having the predicted brightness, the region around the extracted marker 76 can be darkened or lightened to achieve a more uniform lighting of the printed audio format 48.

Initially, a mesh 310 is formed with the luminance of the extracted markers 76 making up the vertices. The luminance within the mesh 310 may be estimated by bi-linearly interpolating from the extracted markers' 76 luminance. Higher ordered interpolation such as, for example, cubic interpolation may also be used. The resulting luminance map can then be used to even out the brightness.

In FIG. 25, the solid circles are the extracted markers 76, and Li denotes their corresponding luminance. The luminance value is the average grey level of the extracted markers or, if it's a colour marker, the Luminance Li=(0.299*Red)+ (0.587*Green)+(0.114*Blue), where Red, Green, and Blue are the average Red, Green, and Blue colour of the marker.

To correct the luminance at arbitrary point P, the following is performed

Let the luminance of the brightest marker be Lmax=max (Li)

The Luminance at point P, Lp can be interpolated from L1, L2, L3, L4 or more neighbouring vertex.

Let the extracted grey level at point P be Gp.

Then the luminance-corrected grey level Gp'=Gp*(Lmax/Lp)

Whilst there has been described in the foregoing description preferred embodiments of the present invention, it will be understood by those skilled in the technology concerned that many variations or modifications in details of design, construction and operation may be made without departing from the present invention.

What is claimed is:

1. A printed audio format comprising:
    a printed encoding of an audio signal; and
    a plurality of spaced-apart and parallel rails,
        the printed encoding of the audio signal is located between the plurality of rails,
        each rail comprises a plurality of markers, the plurality of markers in each rail being distinct from the printed encoding of the audio signal, each marker being selected from a group consisting of solid and hollow,
        each rail being arranged in parallel adjacent a periphery of the printed encoding of the audio signal,
        the printed encoding comprises a first portion and a second portion, each portion comprises a plurality of code frames, each code frame representing a time segment of an audio signal,
        the first portion encodes a first time period of the audio signal and the second portion encodes a second time period of the audio signal, and
        the second portion is encoded in reverse order with respect to the first portion so that a joining part is on a same end of both portions.

2. A printed audio format as claimed in claim 1, wherein the markers in each of the plurality of rails are aligned such that the position of at least two markers can be used for determining positions of all other markers.

3. A printed audio format as claimed in claim 1, wherein at least one marker of the plurality of markers is searchable in at least one of a centre region, an upper region, and a lower region.

4. A printed audio format as claimed in claim 1, wherein the markers are suitable for encoding data.

5. A printed audio format as claimed in claim 1, wherein the audio signal has removed therefrom frequency in the range 0 to 125 Hz prior to encoding.

6. A printed audio format as claimed in claim 1, wherein the encoding is by using at least one of Short Term Fourier Transform and Code Excitation Linear Prediction.

7. A printed audio format as claimed in claim 6, wherein, the encoding is by use of the Short Term Fourier Transform to produce a plurality of frames, every other frame being deleted prior to printing.

8. A printed audio format as claimed in claim 1, wherein the printed encoding is by use of grayscale, each dot of the grayscale having at least one white guard bit in a cellular configuration.

9. A printed audio format as claimed in claim 8, wherein the cellular configuration is a 2×2 cell, the dot being in one segment of the 2×2 cell, all other segments being for guard bits.

10. A printed audio format as claimed in claim 8, wherein the cellular configuration is a 1×2 cell, there being no horizontal guard bit.

11. A printed audio format as claimed in claim 8, wherein a dot of the grayscale is simulated by printing a plurality of small black dots in a specific pattern based on half toning.

12. A printed audio format as claimed in claim 1, wherein the plurality of markers are equally spaced in each rail, the plurality of markers in each rail being distinct from the printed encoding of the audio signal, each marker being selected from the group consisting of: solid and hollow.

13. A printed audio format as claimed in claim 12, wherein there are three rails comprising a top rail, a centre rail, and a bottom rail.

14. A printed audio format as claimed in claim 13, wherein crucial audio data is closer to the centre rail.

15. A printed audio format as claimed in claim 13, wherein the centre rail has markers suitable for encoding digital data.

16. A printed audio format as claimed in claim 15, wherein an audio tag is encoded in the centre rail using solid markers and hollow markers, the audio tag being a unique tag number for identifying an audio clip.

17. A printed audio format as claimed in claim 16, wherein the audio tag is used to search for stored audio in a database, based on the stored audio not being found in the database, the printed encoding of the audio signal is decoded.

18. A printed audio format as claimed in claim 12, wherein the plurality of markers that are distinct from the printed encoding of the audio signal are used for data storage by using solid markers and hollow markers to encode data bits.

19. A printed audio format comprising:
    a printed encoding of an audio signal; and
    a plurality of spaced-apart and parallel rails,
        the printed encoding of the audio signal is located between the plurality of rails,
        each rail comprises a plurality of markers, the plurality of markers in each rail being distinct from the printed encoding of the audio signal, each marker being selected from a group consisting of solid and hollow,
        each rail being arranged in parallel adjacent a periphery of the printed encoding of the audio signal,
        the printed encoding comprises a first portion and a second portion, each portion comprises a plurality of code frames, each code frame representing a time segment of an audio signal,
        the first portion encodes a first time period of the audio signal and the second portion encodes a second time period of the audio signal,
        the second portion is encoded in reverse order with respect to the first portion so that a joining part is on a same end of both portions,
        the encoding is by using at least one of Short Term Fourier Transform and Code Excitation Linear Prediction, and
        based on the encoding being by use of the Short Term Fourier Transform to produce a plurality of frames, every other frame is deleted prior to printing.

* * * * *